United States Patent [19]

Lam et al.

[11] Patent Number: 5,240,910

[45] Date of Patent: Aug. 31, 1993

[54] ANTIHYPERTENSIVE COMPOUNDS PRODUCED BY FERMENTATION

[75] Inventors: Yiu-Kuen T. Lam, Plainsboro; Deborah L. Zink, Manalapan, both of N.J.; David L. Williams, Jr., Hatfield, Pa.

[73] Assignee: Merck & Co., Inc., Rahway, N.J.

[21] Appl. No.: 870,065

[22] Filed: Apr. 17, 1992

[51] Int. Cl.$^5$ .................... A61K 37/02; C07K 7/54
[52] U.S. Cl. .......................... 514/11; 514/9; 514/10; 530/317; 435/71.1
[58] Field of Search .................. 530/317, 321; 514/9, 514/10, 11; 435/71.1

[56] References Cited

U.S. PATENT DOCUMENTS

| | | | |
|---|---|---|---|
| 4,810,692 | 3/1989 | Deschamps et al. | 514/11 |
| 5,138,036 | 8/1992 | Pettit et al. | 530/317 |
| 5,169,862 | 12/1992 | Burke et al. | 530/317 |

FOREIGN PATENT DOCUMENTS 246975  11/1987  European Pat. Off.

OTHER PUBLICATIONS

Yanagisawa et al. (1988) Nature 332, 411–415.
Takagi et al. (1988) Biochem. Biophys. Res. Commun. 157, 1164–1168.
Sugiura et al. (1989) Biochem. Biophys. Res. Commun. 158, 170–176.
Miller et al. (1989) J. Clin. Invest. 83, 317–320.
DuPont Biotech Update (1990).
Warner et al. (1989) J. Cardiovasc. Pharmacol. 13 (Suppl. 5), S85–S88.
Yoshizawa et al. (1990) Science 247, 462–464.
Bousso-Mittler et al. (1989) Biochem. Biophys. Res. Commun. 162, 952–957.
Saito et al. (1989) Hypertension 14, 335–336.
Tomita et al. (1989) New England J. Med. 321, 1127.
Yanagisawa et al. (1989) J. Cardiovasc. Pharmacol. 13 (Suppl. 5) S13–S17.
Sugiura et al. (1989) Biochem. Biophys. Res. Commun. 161, 1220–1227.
Ihara et al., Chem. Abstr. 115, 199551b (1991).

*Primary Examiner*—Herbert J. Lilling
*Attorney, Agent, or Firm*—Sylvia A. Ayler; Mark R. Daniel; Joseph F. DiPrima

[57] ABSTRACT

Novel cyclic depsipeptides derived from a culture of Microbispora are antagonists of the receptor for endothelin, a potent vasoconstrictor, and are thus useful in treating cardiovascular disorders. Endothelin has other physiological effects, and the endothelin receptor antagonists of the present invention thus also have other therapeutic uses. The compounds are cyclical depsipeptides of N-(pyrrol-2-carboxy) - L-phe, D-allo-Thr, D-Phe, D-Ala, D- or L-dihydroxyphenyl-Gly, and D-dihydroxyphenyl-Gly.

2 Claims, No Drawings

ANTIHYPERTENSIVE COMPOUNDS PRODUCED BY FERMENTATION

BACKGROUND OF THE INVENTION

1. Field of the Invention

The present invention belongs to the field of antagonists of the endothelin receptor. Endothelin (ET-1) itself is an endothelium-derived potent vasoconstrictor peptide consisting of 21 amino acids. The unusually prolonged vasoconstriction induced by endothelin in the presence or absence of extracellular $Ca^{2+}$ suggests that the action of this peptide may profoundly influence blood pressure regulation under normal and pathophysiological conditions. As described further below, endothelin also has a number of other physiological effects, and antagonists which bind to its receptor are thus expected to have advantageous pharmacological properties and corresponding therapeutic benefits.

Endothelin Activity and the Effects of Antagonizing Its Receptor Binding

Endothelin (ET-1), and two closely related bioactive peptides, ET-2and ET-3, are widely distributed in mammalian tissues, and they can induce numerous biological responses in non-vascular as well as vascular tissues by binding to at least two distinct endothelin receptor subtypes. In addition to smooth muscle, neural and atrial sites, endothelin receptors may be found in gastrointestinal, urogenital, uteral and placental tissues.

Endothelin is a potent vasoconstrictor peptide and thus plays a role in vivo in arterial pressure-volume homeostasis. Not only peripheral, but coronary vascular resistance as well, is increased by endothelin. Cardiac output is decreased, while plasma renin activity is increased. There is a reduction in renal blood flow and glomerular filtration rate, while levels of atrial natriuretic factor, vasopressin, and aldosterone become elevated.

It is also considered, in accordance with the present invention, that antagonists for the endothelin receptor may be useful in preventing or reducing damage from endothelial denudation following angioplasty. Such denudation results in myointimal thickening following angioplasty, which is caused by increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, cochinmycins IV, and V of the present invention, which are antagonists for the endothelin receptor, have therapeutic usefulness in preventing, decreasing or modulating the various physiological effects of endothelin discussed above, by wholly or partially blocking access of endothein to its receptor.

2. Brief Description of the Prior Art

Endothelin was initially purified from the culture medium of porcine aortic endothelial cells; Yanagisawa et al. (1988) Nature 332, 411–415. Further investigations of the activity of endothelin have been described in publications such as the following:

Takagi et al. (1988) Biochem. Biophys. Res. Commun. 157, 1164–1168.
Sugiura et al. (1989) Biochem. Biophys. Res. Commun. 158, 170–176.
Miller et al. (1989) J. Clin. Invest. 83, 317–320.
Du Pont Biotech Update (1990).
Warner et al. (1989) J. Cardiovasc. Pharmacol. 13(Suppl. 5), S85–S88.
Yoshizawa et al. (1990) Science 247, 462–464.
Bousso-Mittler et al. (1989) Biochem. Biophys. Res. Commun. 162, 952–957.
Saito et al. (1989) Hypertension 14, 335–336.
Tomita et al. (1989) New Engl. J. Med. 321, 1127.
Kurihara et al. (1989) J. Cardiovasc. Pharmacol. 13(suppl. 5) S13–S17.
Sugiura et al. (1989) Biochem. Biophys. Res. Commun. 161, 1220–1227.

U.S. Pat. No. 4,810,692 discloses two immunosuppressant cyclic depsipeptides designated 55185 RP and 59451 RP, although represented by a more general formula which includes many stereoisomers not specified by the formula. While the species 55185RP and 59451RP are characterized by various chemical, physical data, they are nevertheless, unspecified stereoisomers that have been found to be different from cyclic depsipeptides IV and V of the present invention.

The present invention relates to two stereoisomers that, even though one of them, Cochinmycin V, falling within the general formula of the '692 patent, are neither isolated nor suggested in said patent, and are produced by a different microorganism from that in the '692 patent. Cochinmycin IV is another new anolog. Moreover, these two stereoisomers have no immunosuppressant activity. Since the characterization data in the '692 patent is not consistent with the structures proposed therein for the isolated species 55185 RP and 59451 RP, the present invention also relates to the two species described but not enabled in the '692 patent.

U.S. patent application Ser. No. 07/645,535 filed Jan. 24, 1991, describes the isolation of the cyclic depsipeptides I, II, and III (now referred to as cochinmycins I, II, and III) from a fermentation culture of *Microbispora* and the use of cochinmycins I, II and III as endothelin antagonists to treat hypertension. A patent application with Attorney Docket No. 18693, filed concurrently with this application, describes the novel process of making cochinmycins I and v by dechlorination of cochinmycins III and II, respectively.

SUMMARY OF THE INVENTION

The present invention relates to two novel cyclic depsipeptides cochinmycins IV and V active as endothelin receptor antagonists.

The present invention further relates to a method of preparing two novel cyclic depsipeptides IV and V by culturing Microbispora sp. MA6857, ATCC 55140, and isolating the compounds from the fermentation broth.

The present invention relates to a method of treating asthma, hypertension, renal failure particularly post-ischemic renal failure, cyclosporin nephrotoxicity, vasospasm, cerebral and cardiac ischemia, myocardial infarction, or endotoxin shock caused by or associated with endothelin (ET-1), comprising administering to a patient in need of such treatment a therapeutically effective amount of one of two novel cyclic depsipeptides, cochinmycins IV, of V.

The present invention further relates to a pharmaceutical composition for treating asthma, hypertension, renal failure particularly post-ischemic renal failure, cyclosporin nephrotoxicity, vasospasm, cerebral and cardiac ischemia, myocardial infarction, or endotoxin shock caused by or associated with endothelin (ET-1) comprising a therapeutically effective amount of one of two novel cyclic depsipeptides, cochinmycins IV or V together with a pharmaceutically acceptable carrier thereof.

DETAILED DESCRIPTION OF THE INVENTION

In accordance with the present invention there is provided an endothelin receptor antagonist cyclic depsipeptide of the formula:

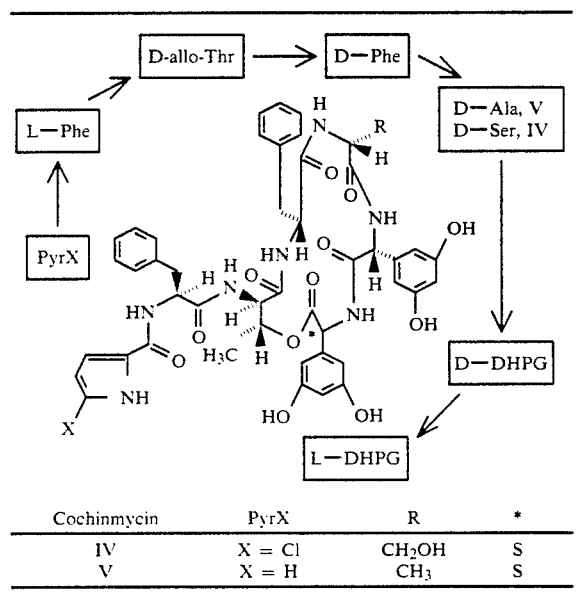

| Cochinmycin | PyrX | R | * |
|---|---|---|---|
| IV | X = Cl | CH$_2$OH | S |
| V | X = H | CH$_3$ | S |

PROTON NUCLEAR MAGNETIC RESONANCE ($^1$H NMR)

The proton nuclear magnetic resonance ($^1$H NMR) spectra for cochinmycins IV and V of the formula above were recorded at 300 MHz in DMSO-d$_6$ on a VARIAN SC300 NMR spectrometer. Chemical shifts were recorded in ppm relative to tetramethylsilane (TMS) at zero ppm using the solvent peak at 2.49 ppm as internal standard. For convenience, the data is presented in tabular form immediately below.

TABLE I $^1$NMR Assignments of Cyclopeptide IV in DMSO-d$_6$ at 30° C. Recorded at 400MHz[a,b]

| Residue | H$_\alpha$ | H$_\beta$ | H$_q$ | H | Aromatic |
|---|---|---|---|---|---|
| D-Ser | 4.02dt J=2.5, 3 | 3.71br s (2H) | — | 8.11d | — |
| D-allo-Thr | 4.33t J=9.5 | 4.97dq J=10, 6 | 1.11d (3H) J=6.5 | 8.69d J=5.5 | — |
| L-Phe | 4.80ddd J=5, 10, 10 | 3.02dd J=5, 13.5 2.87dd J=10.5, 13.5 | — | 8.17d J=7 | 7.15m(5H)[c] |
| D-Phe | 4.55dt J=6, 9 | 3.03dd J=6, 13.5 2.90dd J=9, 13.5 | — | 8.72d J=9 | 7.28m(2H)[c] 7.22m(2H)[c] 7.02m(1H)[c] |

TABLE I-continued $^1$NMR Assignments of Cyclopeptide IV in DMSO-d$_6$ at 30° C. Recorded at 400MHz[a,b]

| Residue | H$_\alpha$ | H$_\beta$ | H$_q$ | H | Aromatic |
|---|---|---|---|---|---|
| L-DHPG | 5.44d J=9 | — | — | 7.72d J=9 | 6.21d(2H) J=2 6.14t J=2 |
| D-DHPG | 5.24d J=7.5 | — | — | 8.25d J=8 | 6.19d(2H) J=2 6.20t J=2 |
| Cl-Pyrrole | — | — | — | 12.21br s | 6.03d 6.90d J=3 |

[a,b,c]See after Table II.

TABLE II $^1$NMR Assignments of Cyclopeptide V in DMSO-d$_6$ at 20° C. Recorded at 300MHz[a,b]

| Residue | H$_\alpha$ | H$_\beta$ | H$_q$ | NH | Aromatic |
|---|---|---|---|---|---|
| D-ala | 3.92dq J=5, 7.5 | 1.32d(3H) J=7.0 | — | 8.22d J=4.5 | — |
| D-allo-Thr | 4.45t J=9.5 | 4.96dq J=10, 6 | 1.11d (3H) J=6 | 8.66d J=9 | — |
| L-Phe | 4.80ddd J=5, 8.5, 9.5 | 3.02dd J=5, 13.5 2.89dd J=10.5, 13.5 | — | 8.12d J=8.5 | 7.14m(5H)[c] |
| D-Phe | 4.49dt J=4, 8, 9 | 3.04dd J=6, 13.5 2.93dd J=9, 13.5 | — | 8.67 J=9.5 | 7.32m(2H)[c] 7.22m(2H)[c] 7.02m(1H)[c] |
| L-DHPG | 5.44d J=9 | — | — | 7.80d J=9 | 6.22d(2H) J=2 6.15t J=2 |
| D-DHPG | 5.24d J=8 | — | — | 8.31d J=8 | 6.18d(2H) J=2 6.19t J=2 |
| Pyrrole | — | — | — | 11.40 (br d) J=2 | 6.06dd J=2.5, 6 6.82m 6.89m |

[a,b,c]See next page.

ABBREVIATIONS: In Tables I and II above, the following abbreviations have been used: s=singlet; d=doublet; t=triplet; m=multiplet; br=broad

CARBON 13 NUCLEAR MAGNETIC RESONANCE ($^{13}$C NMR)

In order to further characterize the cochinmycins IV and V, $^{13}$C NMR spectra were also recorded in DMSO-d$_6$ at 75 MHz on a VARIAN SC300 spectrometer at 20° C., with chemical shifts being given in ppm relative to tetramethylsilane (TMS) at zero ppm using the solvent peak at 39.5 ppm as internal standard. The spectral peaks are indicated below:

Compound IV $^{13}$C NMR Chemical Shifts 16.6, 37.1, 38.2, 53.7, 54.9, 55.7, 56.4, 56.7, 58.4, 60.4, 70.7, 102.0, 102.2, 106.5 (2×), 107.1 (2×), 111.7, 117.2, 125.8, 126.26, 126.35, 128.0(2×), 128.2(2×), 129.1(2×), 129.2(2×), 136.9, 137.8, 138.4, 139.4, 158.1 (2×), 158.2 (2×), 159.1, 168.3, 168.5, 169.0, 170.0, 171.4, 171.5 ppm.

Compound V $^{13}$C NMR Chemical Shifts 16.6, 16.9, 36.7, 38.0, 51.9, 53.9, 55.0, 55.8, 56.1, 56.2 70.7, 101.9, 102.1, 106.6 (2×), 106.9 (2×), 108.6, 110.7, 121.5, 125.8, 126.2, 126.3, 128.0 (2×), 128.2 (2×), 129.1 (2×), 129.2 (2×), 137.0, 138.0, 138.3, 139.7, 158.0 (2×), 158.2 (2×), 160.2, 168.4, 168.7, 168.9, 171.2, 171.7, 172.3 ppm.

Stereochemistry

Comparison of $^1$H- and $^{13}$C-NMR data with earlier reported cochinmycins (disclosed in U.S. patent application Ser. No. 07/645,535 filed Jan. 24, 1991) suggested that cochinmycins IV and V are new members of this family. Of importance, stereochimcally they were cochinmucin II-like rather than cochinmycin III-like. Also, both cochinmycins IV and V are dextrorotatory.

GC-MS analysis of cochinmycin IV identified Ser, allo- Thr, Phe and DHPG. The AMBI analysis of the total acid hydrolysate indicated 1×D-allo-Thr, 1×D-Ser, 1×L-DHPG, 1×D-DHPG, 1×Phe. The Phe in the macrolactone portion was assigned as D-Phe based on components reported earlier (disclosed in U.S. patent application Ser. No. 07/645,535 filed Jan. 24, 1991).

GC-MS analyses were performed on the trimethylsilyl derivatives (prepared with a 1:1 mixture of BSTFA-pyridine at 50° C. for 30 minutes) of the total acid hydrolysate (6N HCl at 100° C. for 18 hours) of each component.

Amino acid enantiomers were differentiated using the α-methylbenzylisothiocyanate (AMBI) method with standard reference amino acids. In all cases, the L enantiomers eluted earlier than the corresponding D enantiomers.

The absolute stereochemistry of cochinmycin V was further established by identity with the deschlorination product of cochinmycin II (disclosed in Attorney Docket No. 18693 filed concurrently with this application).

Cochinmycins IV and V thus have the stereochemistries shown in the formula below:

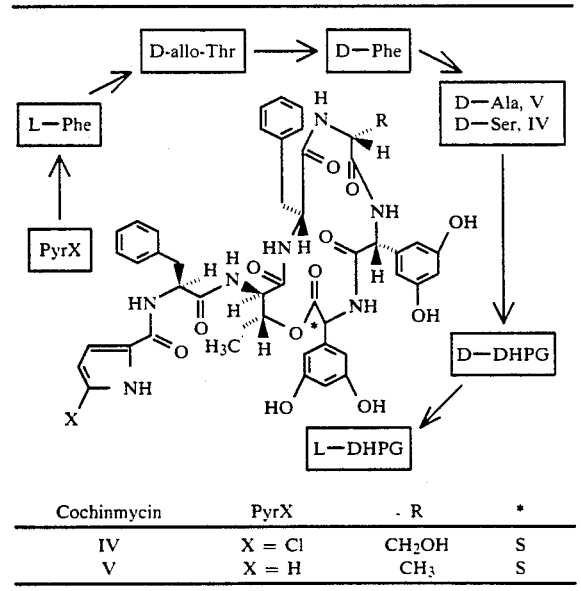

| Cochinmycin | PyrX | R | * |
|---|---|---|---|
| IV | X = Cl | CH$_2$OH | S |
| V | X = H | CH$_3$ | S |

The following table sets forth the physico-chemical and biochemical characteristics of cochinmycins IV and V:

TABLE III

Physico-chemical and biochemical characteristics of cochinmycins IV and V.

| | Cochinmycin IV | Cochinmycin V |
|---|---|---|
| Molecular Formula | C$_{46}$H$_{46}$N$_7$O$_{13}$Cl | C$_{46}$H$_{47}$N$_7$O$_{12}$ |
| HR-FAB-MS$^a$((M+H)$^+$m/z) | | |
| Found: | 940.2921 | 890.3360 |
| Calcd: | 940.2920 | 890.3361 |
| [α]$_D^{23b}$ | +30.0° (c 0.1 in MeOH) | +20.0° (c 0.1 in MeOH) |
| UV$_{max}$$^{c\lambda MeOH}$ nm(E %) | 214(485), 229(sh, 240), 274(234) | 214(489), 230(sh, 237 270(224) |
| FT-IR$^d$(ZnSe)$^\nu$max$^{cm-1}$ | 3309, 1738, 1661, 1607, 1525 | 3302, 1739, 1661, 1555, 1516 |
| HPLC$^e$t$_R$ (minutes) | 4.4 | 3.3 |
| [$^{125}$I]endothelin binding: IC$_{50}$ (μM) | | |
| cow aorta | 3 | 90 |
| rat hippocampus | 2 | 25 |

$^a$JOEL HX110 mass spectrometer at 10 kV using ULTRAMARK 1621 as the internal standard.
$^b$Perkin-Elmer 241 polarimeter.
$^c$Beckman DU-70 ultraviolet spectrophotometer.
$^d$Perkin-Elmer 1750 FOURIER transform infrared spectrophotometer: sample deposited on a zinc selenide crystal at ambient temperature.
$^e$Whatman PARTISIL 5 ODS-3, 4.6 × 100 mm; MeOH - H$_2$O(45:55); flow rate, 1 ml/minute; 40° C.; detection - UV 215 nm.
sh = Shoulder

Fermentation of Microbispora sp. MA 6857

Cochinmycins IV, and V of the present invention were isolated from a culture of a strain of Microbispora which is novel and which has been designated sp. MA6857. A sample of this microorganism was deposited under the Budapest Treaty at the American Type Culture Collection (ATCC), 12301 Parklawn Drive, Rockville, Md. 20852, on Jan. 17, 1991, where it has been assigned the accession number ATCC 55140. Any restrictions related to the public access of the microorganism shall be irrevocably removed upon a patent grant. Based on the macro and micromorphology, the microorganism is a member of the genus Microbispora which is characterized by the formation of paired spores borne on an aerial mycelium. However, the microorganism has taxonomic and other features which distinguish it from the known strains of the genus Microbispora, and on that basis it is believed to be a novel. It has, consequently, been designated herein Microbispora sp. MA6857.

The microorganism Microbispora sp. MA6857 was isolated from a culture prepared by well known methods from a soil sample originating in Cochin, India. In order to produce scaled-up culture batches for supplying quantities of cochinmycins IV, and V, a seed culture was produced by inoculating 50 ml of aqueous nutrient medium, ATCC, in a 250 ml triple baffled erlenmeyer flask with 2 ml of refrigerated or thawed frozen vegatative mycelia. The nutrient medium ATCC has the following composition:

| ATCC | | |
|---|---|---|
| Glucose | 10.0 g | pH adjusted to 7.0 with |
| Soluble starch | 20.0 g | NaOH prior to CaCO$_3$ |
| Yeast extract | 5.0 g | addition |
| N—Z amine E | 5.0 g | |
| CaCO$_3$ | 1.0 g | |
| Beef extract | 3.0 g | |
| BACTO-PEPTONE | 5.0 g | |

The culture vessel was incubated at 28° C. and shaken at 220 rpm for 96 hrs in order to obtain sufficient biomass for use as an inoculum for the preparation of second stage seed. Four milliliters of the 96 hour culture was aseptically transferred to 500 ml of the same nutrient medium, ATCC, in a 2-liter baffled flask and incubated at 28° C. on a 220 rpm rotary shaker for 72 hours in order to obtain sufficient biomass for use as an inoculum for production medium. The production medium employed, SAM-4, contained sources of assimilable organic nutrients for growth of the culture in the form of dextrin, soybean flour and peptone. Its composition is set out below:

| SAM-4 | | |
|---|---|---|
| Dextrin | 50.0 g | pH adjusted to 7.0 with |
| Soybean flour | 30.0 g | NaOH prior to CaCO3 |
| DIFCO PEPTONE | 1.0 g | addition |
| CaCO3 | 5.0 g | |
| Distilled H2O | 1000 ml | |

1500 ml of this second seed culture was used in each 75-liter stainless steel fermenters containing 50 liters of the production medium. The fermentation was carried out at 25° C. and pH 6.4-7.3, under an aeration of 15 liters/minute, and a stirrer speed of 400 to 500 rpm for 9 to 10 days.

Isolation of Cochinmycins II, III, IV, and V

The whole broth from two fermenters (100 liters) was immediately extracted with methylethyl ketone (2×100 liters). Flash evaporation of the methylethyl ketone layer to dryness under reduced pressure at 40° C. gave 245 g of crude extract. This crude extract was mixed with dichloromethane (850 ml) and adsorbed on to an open column of 2.5 kg silica gel 60 (E. Merck, 0.2–0.5 mm particle size) in the same solvent. Stepwise gradient elution with 7, 25, and 24 liters of 0, 5, and 10% methanol/dichloromethane respectively, afforded 32.6 g of cochinmycin enriched fraction in the 10% methanol/dichloromethane effluent. In this exercise, this enriched fraction was purified as two injections on a Separations Technology C-18 Column (7.6×91 cm, 0.02 mm particle size) using 55% methanol (aq) as the mobile phase for elution at 200 ml/minute and room temperature, monitoring at 270 nm. At this step, in order of elution, 0.66 g of enriched cochinmycin V, 0.19 g of homogeneous cochinmycin IV, 16 g of cochinmycin II and 1.47 g of cochinmycin III were recovered at elution volumes of 9.2–11.5, 17.4–19.2, 22.5–30.7, and 39.0–47.7 liters, respectively. Thus, using the present procedure, cochinmycins II, III, and IV can be isolated in two chromatographic steps from whole broth.

The cochinmycin V enriched fraction above was purified as one sample on a Whatman PARTISIL 10 ODS-3 column (2.21×50 cm). Elution was performed with 45% methanol (aq) at 15 ml/minute and room temperature. The effluent was monitored at 215 nm. Homogeneous cochinmycin V (0.49 g) was recovered from elution volumes of 480–675 ml.

Endothelin receptor Binding Assay Results

The binding of cochinmycins IV and V to the endothelin receptor was determined in accordance with the assay described in detail immediately below. It is similar to the assay described in Ambar et al. (1989) Biochem. Biophys. Res. Commun. 158, 195–201; and Kloog et al. (1989) Febs Letters, 253, 199–202.

Endothelin-1 (ET-1) was purchased from Peptides International (Louisville, Ky.). $^{125}$I-ET-1(2000 Ci/mMol) was purchased from Amersham (Arlington Heights, Ill.).

Membranes were prepared from rat hippocampus, and rat or cow aorta. Dissected tissue was homogenized twice for 30 seconds with a Brinkman POLYTRON [setting 10, Generator PTA 20 TS (Westbury, N.Y.)] in ice cold 250 mM sucrose, 50 mM Tris-HCl pH 7.4 with 7 μg/ml pepstatin A and 0.5 μg/ml leupeptin. The crude particulate matter was removed by centrifugation at 750×g for 10 min. The membranes were sedimented from the supernatant fraction by centrifugation at 48,000 g for 30 min. Membrane pellets were resuspended in the above buffer with protease inhibitors. Aliquots of these suspensions were stored at −70° C.

Binding studies with $^{125}$I-ET-1 were conducted in 50 mM potassium phosphate pH 7.5 with 0.1% bovine serum albumin (BSA) using 12-well SKATRON (Lier, Norway) cell harvester tube strips. $^{125}$I-ET-1 concentrations were 25 pM for hippocampus, 150 pM for aorta. Samples were dissolved in dimethylsulfoxide (DMSO). Upon addition of the sample, the final DMSO concentration was 3%. Membranes were added last to start the binding reaction. The reaction mixture was incubated at 37° C. for 30 or 60 minutes. Binding reactions were terminated using a SKATRON cell harvester by filtration through glass fiber filter pads presoaked with 2% BSA. The samples on the pads were immediately washed with 150 mM NaCl 0.1% BSA. The pads were punched out and radioactivity was evaluated in a Beckman GAMMA 5500 gamma counter (Fullerton, Calif.). Nonspecific binding was determined in the presence of 100 nM ET-1. The results of this binding assay are set out in the table of values below:

TABLE IV

| Affinity for ET-A and ET-B Receptors | | |
|---|---|---|
| | $K_i$ (nM) vs. [$^{125}$I]-ET-1 | |
| | Cow Aorta (ET-A) | Rat Hippocampus (ET-B) |
| Cochinmycin IV | 300 | 200 |
| Cochinmycin V | 9000 | 2500 |

In accordance with the present invention, cochinmycins IV and V are useful in human therapy for treating asthma, hypertension, renal failure particularly post-ischemic renal failure, cyclosporin nephrotoxicity, vasospasm, cerebral and cardiac ischemia, myocardial infarction, or endotoxic shock, comprising administering to a human patient in need of such treatment, a therapeutically effective amount of cyclic depsipeptides IV and V.

The particular dosage to be administered in the course of such treatment is the result of a number of factors, such as the particular condition being treated, the route of administration, the age, sex, weight and general condition of the patient being treated, and whether acute or chronic treatment is envisioned. With those considerations in mind, it can be stated that, as a general matter, cochinmycins IV and V of the present invention will be administered orally to a patient in dosage amounts between 1 and 200 mg/kg/day, and will be administered parenterally to a patient in dosage amounts between 0.5 and 100 mg/kg/day.

The present invention also relates to pharmaceutical compositions for treating asthma, hypertension, renal failure particularly post-ischemic renal failure, cyclosporin nephrotoxicity, vasospasm, cerebral and cardiac ischemia, myocardial infarction, or endotoxin shock caused by or associated with endothelin, comprising a therapeutically effective amount of cochinmycins IV or V together with a pharmaceutically acceptable carrier therefor.

Where the pharmaceutical compositions of the present invention are for oral administration, e.g., as tablets, the active ingredient, i.e., cochinmycins IV or V, will be used in combination with other compounding ingredients such as talc, vegetable oils, polyols, benzyl alcohols, gums, gelatins, starches and other carriers, all of which are well known in the art. Where the pharmaceutical compositions of the present invention are for parenteral administration, the active ingredient will be dissolved or dispersed in a suitable liquid carrier, or emulsions may be formed using suitable emulsifying agents.

What is claimed is:

1. A cyclic depsipeptide endothelin antagonist of the formula:

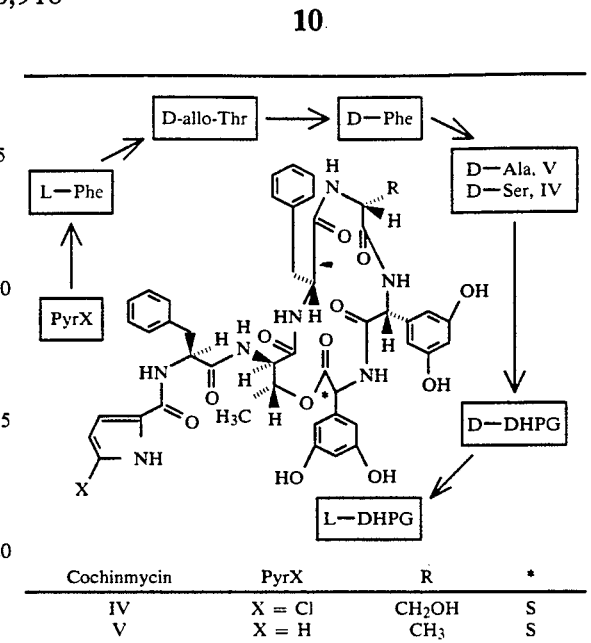

| Cochinmycin | PyrX | R | * |
|---|---|---|---|
| IV | X = Cl | CH$_2$OH | S |
| V | X = H | CH$_3$ | S | in substantially pure form.

2. A method of treating asthma, hypertension, renal failure cyclosporin nephrotoxicity, vasospasm, cerebral and cardiac ischemia, myocardial infarction, or endotoxin shock caused by or associated with endothelin, comprising administering to a patient in need of such treatment, a therapeutically effective amount of a cyclic depsipeptide IV or V of claim 1.

* * * * *